United States Patent
Puleo et al.

(10) Patent No.: US 9,616,361 B2
(45) Date of Patent: *Apr. 11, 2017

(54) SYSTEMS FOR SEPARATION OF PARTICULATES AND ASSOCIATED METHODS AND DEVICES

(71) Applicant: GENERAL ELECTRIC COMPANY, Schenectady, NY (US)

(72) Inventors: Christopher Michael Puleo, Niskayuna, NY (US); Jason Louis Davis, Albany, NY (US); Jason M. Nichols, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 456 days.

This patent is subject to a terminal disclaimer.

(21) Appl. No.: 14/243,469

(22) Filed: Apr. 2, 2014

(65) Prior Publication Data
US 2015/0165346 A1 Jun. 18, 2015

Related U.S. Application Data

(60) Provisional application No. 61/916,379, filed on Dec. 16, 2013.

(51) Int. Cl.
*B01D 21/02* (2006.01)
*B01D 21/24* (2006.01)
(Continued)

(52) U.S. Cl.
CPC ......... *B01D 21/0087* (2013.01); *B01D 17/02* (2013.01); *B01D 21/0006* (2013.01);
(Continued)

(58) Field of Classification Search
CPC B01D 21/0087; B01D 17/02; B01D 21/2433; B01D 21/0042; B01D 21/2444;
(Continued)

(56) References Cited

U.S. PATENT DOCUMENTS 4,197,847 A 4/1980 Djerassi
4,737,268 A * 4/1988 Giddings ........... G01N 30/0005
209/12.2

(Continued)

FOREIGN PATENT DOCUMENTS

EP 0730639 B1 4/2003
WO 2011079217 A1 6/2011

OTHER PUBLICATIONS

Yue et al., "Miniature Field-Flow Fractionation System for Analysis of Blood Cells", Cunical Chemistry, pp. 1810-1814, vol. 40, Issue 9, 1994.

(Continued)

*Primary Examiner* — Joseph Drodge
(74) *Attorney, Agent, or Firm* — Pabitra K. Chakrabarti

(57) ABSTRACT

A system is provided for separating particulates dispersed within a base fluid wherein at least one of the particulates and the base fluid is an organic liquid. The system relies on a microfluidic separation device comprising a microchannel in fluid communication across a microporous body with a collection chamber. Particulates and a portion of the base fluid traverse the microporous body under the influence of an external force field and are collected in the collection chamber. A first fluid flow having a first flow rate through the microchannel together with the microporous body operationally generate a second fluid flow within the collection chamber as base fluid and particulates traverse the microporous body and enter the collection chamber, and as base fluid re-traverses the microporous body and re-enters the microchannel, the second fluid flow having a flow rate which is a fraction of the first flow rate.

25 Claims, 12 Drawing Sheets

(51) Int. Cl.
| | |
|---|---|
| *B01D 21/28* | (2006.01) |
| *C02F 1/24* | (2006.01) |
| *C02F 1/48* | (2006.01) |
| *B01D 21/00* | (2006.01) |
| *C02F 1/00* | (2006.01) |
| *C12M 1/00* | (2006.01) |
| *C12N 5/078* | (2010.01) |
| *B01L 3/00* | (2006.01) |
| *B01D 17/02* | (2006.01) |
| *C02F 103/08* | (2006.01) |
| *C02F 103/10* | (2006.01) |
| *C02F 1/44* | (2006.01) |
| *C02F 101/32* | (2006.01) |

(52) U.S. Cl.
CPC ......... *B01D 21/0042* (2013.01); *B01D 21/10* (2013.01); *B01D 21/245* (2013.01); *B01D 21/2433* (2013.01); *B01D 21/2444* (2013.01); *B01L 3/502753* (2013.01); *B01L 3/502761* (2013.01); *C02F 1/00* (2013.01); *C02F 1/24* (2013.01); *C12M 47/02* (2013.01); *C12N 5/0641* (2013.01); *B01D 21/02* (2013.01); *B01D 2221/04* (2013.01); *B01L 2200/0631* (2013.01); *B01L 2200/0652* (2013.01); *B01L 2200/0668* (2013.01); *B01L 2300/0681* (2013.01); *B01L 2300/0851* (2013.01); *B01L 2400/043* (2013.01); *B01L 2400/0421* (2013.01); *B01L 2400/0457* (2013.01); *B01L 2400/0469* (2013.01); *C02F 1/444* (2013.01); *C02F 1/48* (2013.01); *C02F 2001/007* (2013.01); *C02F 2101/32* (2013.01); *C02F 2103/08* (2013.01); *C02F 2103/10* (2013.01); *C02F 2201/002* (2013.01)

(58) Field of Classification Search
CPC .. B01D 21/10; B01D 21/0006; B01D 21/245; B01D 11/02; B01D 11/0211; B01D 11/0207; B01D 17/0217; B01D 17/12; B01D 17/16; B01D 21/26; B01D 21/30; B01D 21/34; B01D 61/14; B01D 61/18; B01D 61/20; B01D 61/22; B01D 61/42; B01D 61/425; B01D 61/427; B01D 61/54; B01D 61/58; B01D 63/08; B01D 63/088; B01D 2311/16; B01D 2311/26; B01D 2311/2603; B01D 2311/2607; B01D 2311/2646; B01D 2311/2676; B01D 2200/0631; B01D 2200/14; B01D 17/0208; B01D 17/06; B01D 21/24; B01D 21/28; B01L 3/502753; B01L 3/502761; B01L 3/5027; B01L 3/502715; B01L 3/50273; B01L 3/502746; C12N 5/0641; C12M 47/02; C02F 1/00; C02F 1/24; C02F 1/48; G01N 30/0005; G01N 30/0015; G01N 30/002; G01N 30/007
USPC ................ 73/863.21, 863.23; 204/518, 519, 204/542–545, 553, 601, 602, 627, 628; 210/143, 223, 243, 321.6, 321.75, 321.84, 210/511, 513, 644, 645, 649, 650, 651, 210/748.01, 748.05, 695, 800, 802, 222
See application file for complete search history.

(56) References Cited

U.S. PATENT DOCUMENTS

| | | | | |
|---|---|---|---|---|
| 4,927,535 A * | 5/1990 | Beck | ...................... | B01D 63/02 210/500.23 |
| 5,011,022 A * | 4/1991 | Palepu | ................... | B01D 43/00 209/155 |
| 5,277,774 A * | 1/1994 | Shmidt | ............ | G01N 27/44773 204/450 |
| 5,282,982 A | 2/1994 | Wells | | |
| 5,789,148 A | 8/1998 | Van Vlasselaer et al. | | |
| 5,961,832 A * | 10/1999 | Shaw | ................. | B01D 11/0415 210/243 |
| 5,971,158 A * | 10/1999 | Yager | .................... | B01J 19/0093 209/155 |
| 6,454,945 B1 | 9/2002 | Weigl et al. | | |
| 6,641,708 B1 * | 11/2003 | Becker | .................... | B03C 5/026 204/547 |
| 7,264,608 B2 | 9/2007 | Bischof et al. | | |
| 7,276,170 B2 * | 10/2007 | Oakey | .................... | B01D 57/02 204/451 |
| 8,097,153 B2 | 1/2012 | Leonard et al. | | |
| 8,157,774 B1 | 4/2012 | Altobelli | | |
| 8,241,592 B2 | 8/2012 | Duffy et al. | | |
| 8,263,359 B2 | 9/2012 | Reschiglian et al. | | |
| 8,361,321 B2 * | 1/2013 | Stetson | ................. | B01D 61/02 210/257.2 |
| 8,470,180 B2 | 6/2013 | Leonard et al. | | |
| 8,535,536 B1 * | 9/2013 | Gale | ...................... | B01D 57/00 210/198.1 |
| 9,250,163 B2 * | 2/2016 | Gadini | ............. | B01L 3/502753 |
| 2002/0084221 A1 | 7/2002 | Verkaart et al. | | |
| 2004/0019300 A1 | 1/2004 | Leonard | | |
| 2004/0072278 A1 * | 4/2004 | Chou | ................ | B01L 3/502761 435/29 |
| 2005/0148064 A1 * | 7/2005 | Yamakawa | ....... | B01L 3/502761 435/287.2 |
| 2008/0035541 A1 * | 2/2008 | Franzreb | .............. | B01D 61/002 210/137 |
| 2008/0257071 A1 * | 10/2008 | Wimberger-Friedl | | B01L 3/5027 73/863.23 |
| 2012/0085649 A1 * | 4/2012 | Sano | ....................... | B03C 5/005 204/547 |
| 2012/0234731 A1 | 9/2012 | Senftleber | | |
| 2012/0298579 A1 * | 11/2012 | Jablonski | ........... | B01D 17/0202 210/643 |
| 2013/0086980 A1 * | 4/2013 | Gadini | ............. | B01L 3/502753 73/61.71 |
| 2013/0168250 A1 * | 7/2013 | Fogleman | ......... | B01L 3/502792 204/547 |

OTHER PUBLICATIONS

Assidjo et al., "Osmolarity Effects on Red Blood Cell Elution in Sedimentation Field-Flow Fractionation", Journal of Chromatographic Science, pp. 229-236, vol. 37, Issue 7, Jul. 1999.
Zheng et al., "Membrane Microfilter Device for Selective Capture Electrolysis and Genomic Analysis of Human Circulating Tumor Cells", J Chromatogr A, pp. 154-161, vol. 1162, Issue 2, Aug. 2007.
Brune et al., "Quality, Stability and Safety Data of Packed Red Cells and Plasma Processed by Gravity Separation Using a New Fully Integrated Hollow-Fibre Filter Device", Advances in Hematology, pp. 1-6, vol. 2010, 2009.
Roda et al., "Field-Flow Fractionation in Bioanalysis a Review of Recent Trends", Analytica Chimica Acta, pp. 132-143, vol. 635, Issue 2, Mar. 2009.
Kersaudy-Kerhoas et al., "Validation of a Blood Plasma Separation System by Biomarker Detection", Lab on a Chip, pp. 1587-1595, vol. 10, Issue 12, 2010.
Gossett et al., "Label-Free Cell Separation and Sorting in Microfluidic Systems", Anal Bioanal Chem, pp. 3249-3267, vol. 397, Issue 8, Aug. 2010.
Dimov et al., "Stand-Alone Self-Powered Integrated Microfluidic Blood Analysis System (SIMBAS)", Lab on a Chip, pp. 845-850, vol. 11, Issue 5, 2011.
Bhagat et al., "Pinched Flow Coupled Shear-Modulated Inertial Microfluidics for High-Throughput Rare Blood Cell Separation", Lab on a Chip, pp. 1870-1878, vol. 11, Issue 11, 2011.
Lim et al., "Visualization of Microscale Particle Focusing in Diluted and Whole Blood Using Particle Trajectory Analysis", Lab on a Chip, pp. 2199-2210, vol. 12, Issue 2, 2012.

(56) References Cited

OTHER PUBLICATIONS

Udara R. Dharmasiri, "Highly Efficient Selection, Enumeration, Enrichment, and Molecular Profiling of Low-Abundant Biological Cells", 202 Pages.

* cited by examiner

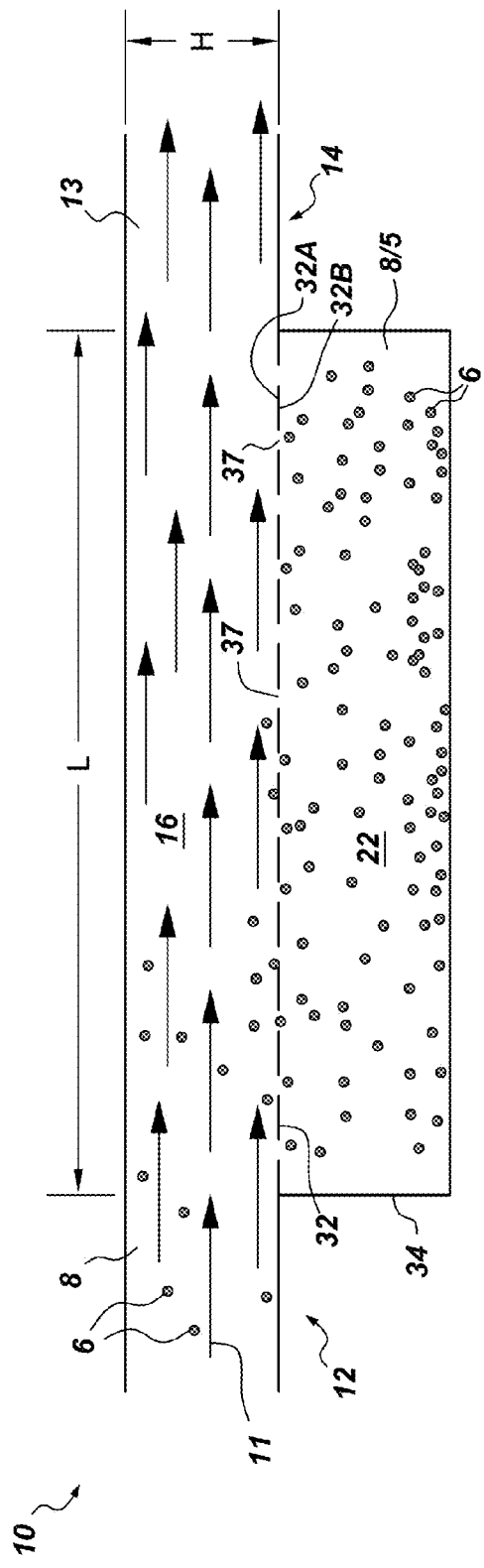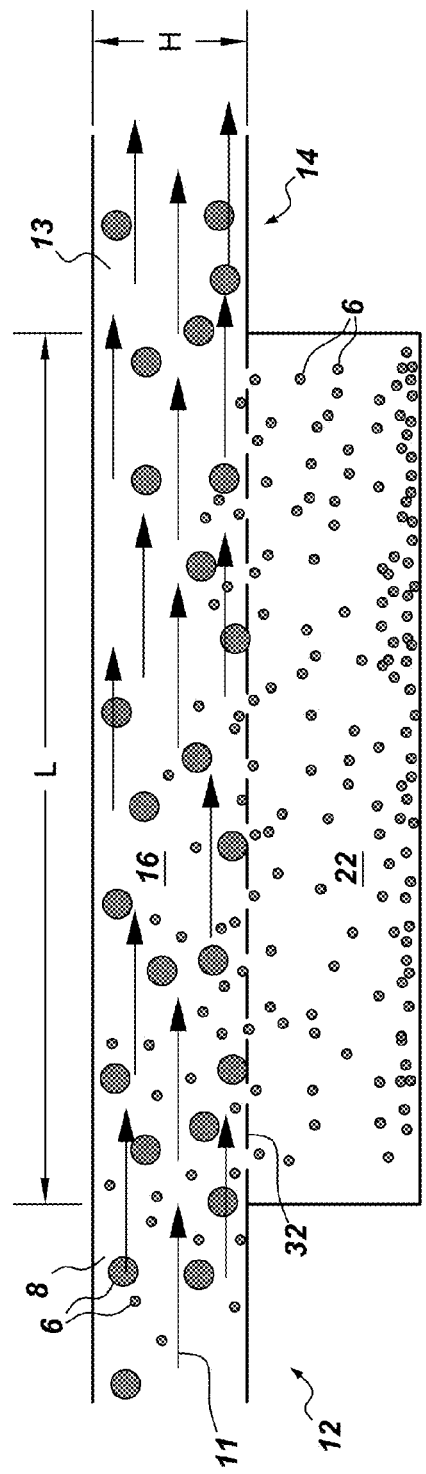

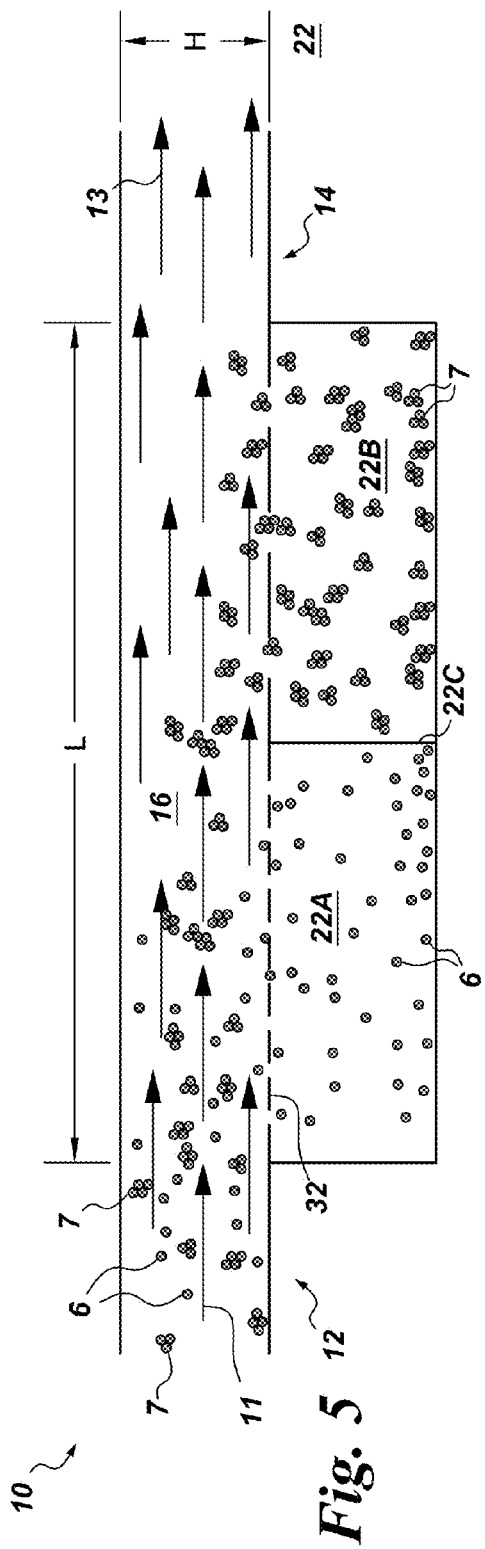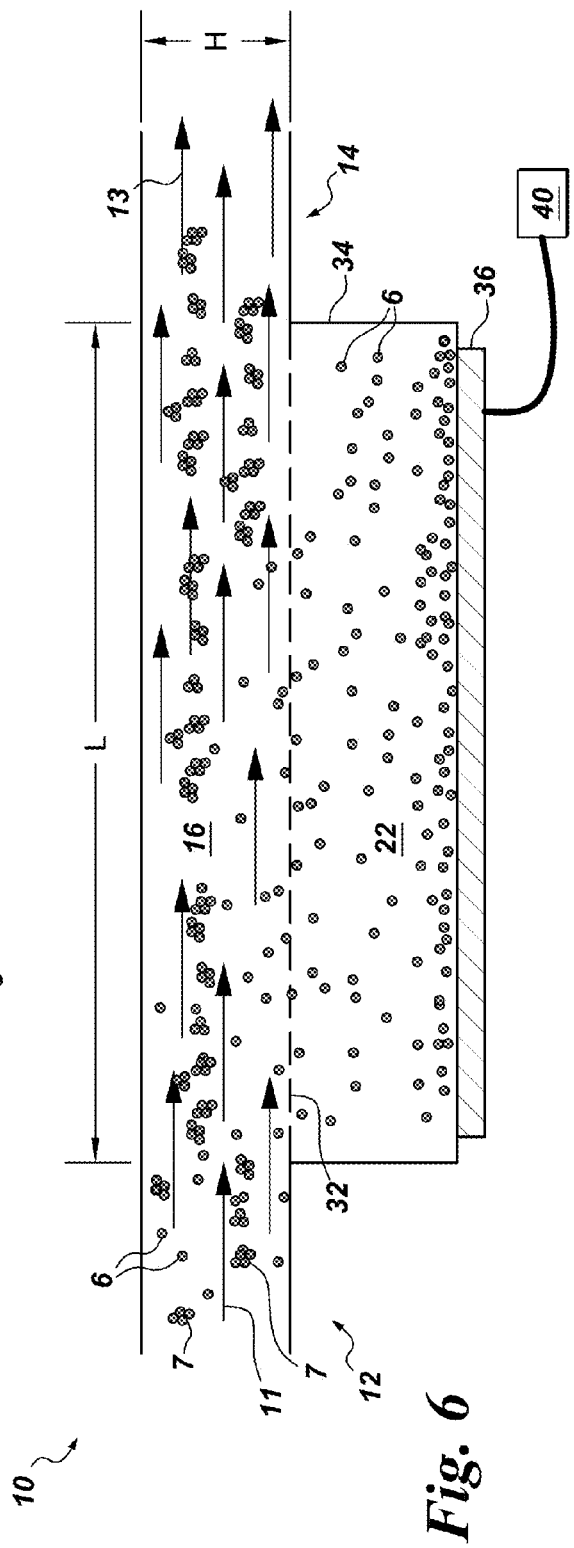

SYSTEMS FOR SEPARATION OF PARTICULATES AND ASSOCIATED METHODS AND DEVICES

CROSS REFERENCE TO RELATED APPLICATIONS

This application claims the benefit of U.S. Provisional Application No. 61/916,379, entitled "Systems for Separation of Particulates and Associated Methods and Devices", filed Dec. 16, 2013, and which is incorporated herein by reference in its entirety.

BACKGROUND

The invention relates to microfluidic separation systems, devices and methods useful for separating particulate materials from fluids. In a particular aspect, the invention relates to a method for separating organic liquids from fluid mixtures comprising such organic liquids.

While a substantial body of knowledge pertaining to the separation of organic liquids from aqueous liquids has been developed in concert with the continuing evolution of foodstuff manufacturing, chemical manufacturing and oil production techniques, further enhancements and efficiencies are needed.

BRIEF DESCRIPTION

In one embodiment, the present invention provides a system for separating particulates dispersed within a base fluid, the system comprising: a fluid inlet; a fluid outlet; a microchannel disposed between the fluid inlet and fluid outlet; a microporous body defining at least a portion of the microchannel; and a collection chamber on an opposing side of the microporous body; the system being configured such that the particulates and a portion of the base fluid traverse the microporous body under the influence of an external force field and are collected in the collection chamber; and such that a first fluid flow having a first flow rate through the microchannel together with the microporous body operationally generate a second fluid flow within the collection chamber as base fluid and particulates traverse the microporous body and enter the collection chamber, and as base fluid re-traverses the microporous body and re-enters the microchannel, the second fluid flow having a flow rate which is a fraction of the first flow rate; and such that at least one of the particulates and the base fluid comprises an organic liquid.

In an alternate embodiment, the present invention provides a system for separating organic liquid particulates dispersed in an aqueous base fluid, the system comprising: a fluid inlet; a fluid outlet; a microchannel disposed between the fluid inlet and fluid outlet; a microporous body defining at least a portion of the microchannel; and a collection chamber on an opposing side of the microporous body; the system being configured such that the particulates and a portion of the aqueous base fluid traverse the microporous body under the influence of an external force field and are collected in the collection chamber; and such a first fluid flow having a first flow rate through the microchannel together with the microporous body operationally generate a second fluid flow within the collection chamber as aqueous base fluid and particulates traverse the microporous body and enter the collection chamber, and as the aqueous base fluid re-traverses the microporous body and re-enters the microchannel, the second fluid flow having a flow rate which is a fraction of the first flow rate.

In another embodiment, the present invention provides a system for separating particulates dispersed in an organic base fluid, the system comprising: a fluid inlet; a fluid outlet; a microchannel disposed between the fluid inlet and fluid outlet; a microporous body defining at least a portion of the microchannel; and a collection chamber on an opposing side of the microporous body; the system being configured such that the particulates and a portion of the hydrocarbon base fluid traverse the microporous body under the influence of an external force field and are collected in the collection chamber; and such that a first fluid flow having a first flow rate through the microchannel together with the microporous body operationally generate a second fluid flow within the collection chamber as base fluid and particulates traverse the microporous body and enter the collection chamber, and as base fluid re-traverses the microporous body and re-enters the microchannel, the second fluid flow having a flow rate which is a fraction of the first flow rate.

In yet another embodiment, the present invention provides a method for separating particulates dispersed within a base fluid, the method comprising: (a) providing a separation device comprising: (i) a fluid inlet; (ii) a fluid outlet; (iii) a microchannel disposed between the fluid inlet and the fluid outlet; (iv) a microporous body defining at least a portion of the microchannel; and (v) a collection chamber on an opposing side of the microporous body; (c) introducing via the fluid inlet a stream of unprocessed fluid comprising particulates dispersed within a base fluid into the microchannel; (d) separating at least a portion of the particulates from the unprocessed fluid to provide a stream of processed fluid at the fluid outlet; and (e) recovering in the collection chamber at least a portion of the particulates initially present in the unprocessed fluid; wherein the particulates dispersed in the base fluid together with a portion of the base fluid under the influence of an external force field traverse the microporous body and are collected in the collection chamber and are separated from the fluid flowing through the microchannel; wherein a first fluid flow having a first flow rate through the microchannel together with the microporous body operationally generate a second fluid flow within the collection chamber as base fluid and particulates traverse the microporous body and enter the collection chamber, and as base fluid re-traverses the microporous body and re-enters the microchannel, the second fluid flow having a flow rate which is a fraction of the first flow rate; and wherein at least one of the particulates and the base fluid comprises an organic liquid.

DRAWINGS

These and other features, aspects, and advantages of the present invention will become better understood when the following detailed description is read with reference to the accompanying drawings in which like characters represent like parts throughout the drawings, wherein:

FIG. 3 illustrates a separation system provided by the present invention and a method for using such separation system.

FIG. 4 illustrates a separation system provided by the present invention and a method for using such separation system.

FIG. 5 illustrates a separation system provided by the present invention and a method for using such separation system.

FIG. 6 illustrates a separation system provided by the present invention and a method for using such separation system.

Figure 13:
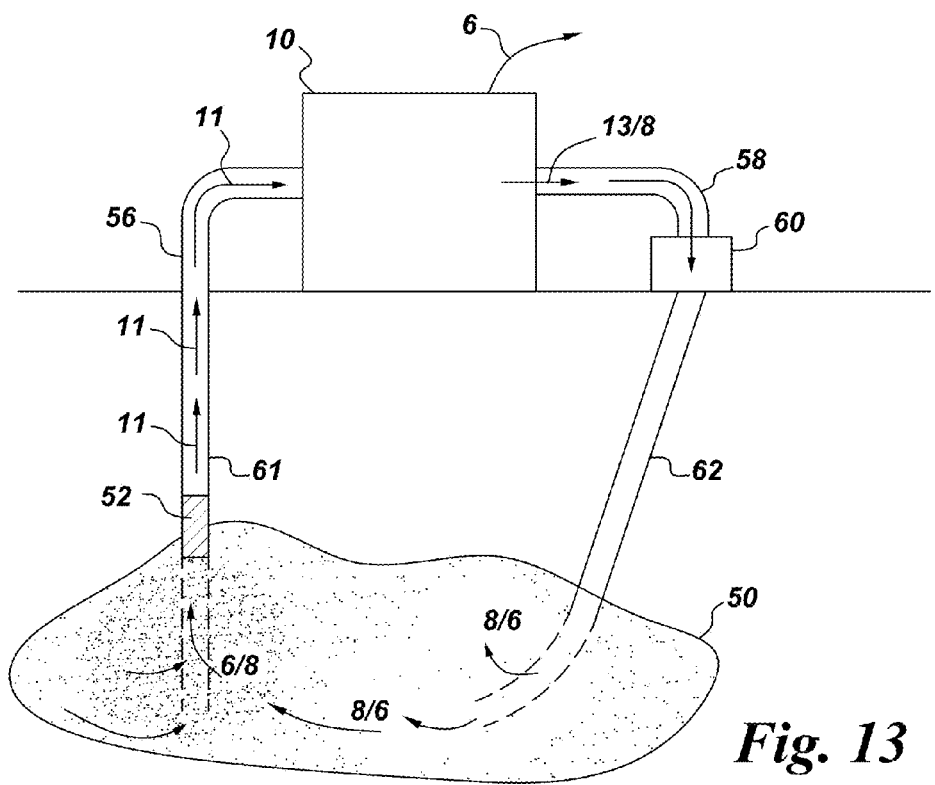
FIG. 13 illustrates a deployed separation system provided by the present invention and a method for using such separation system.
Figure 14:
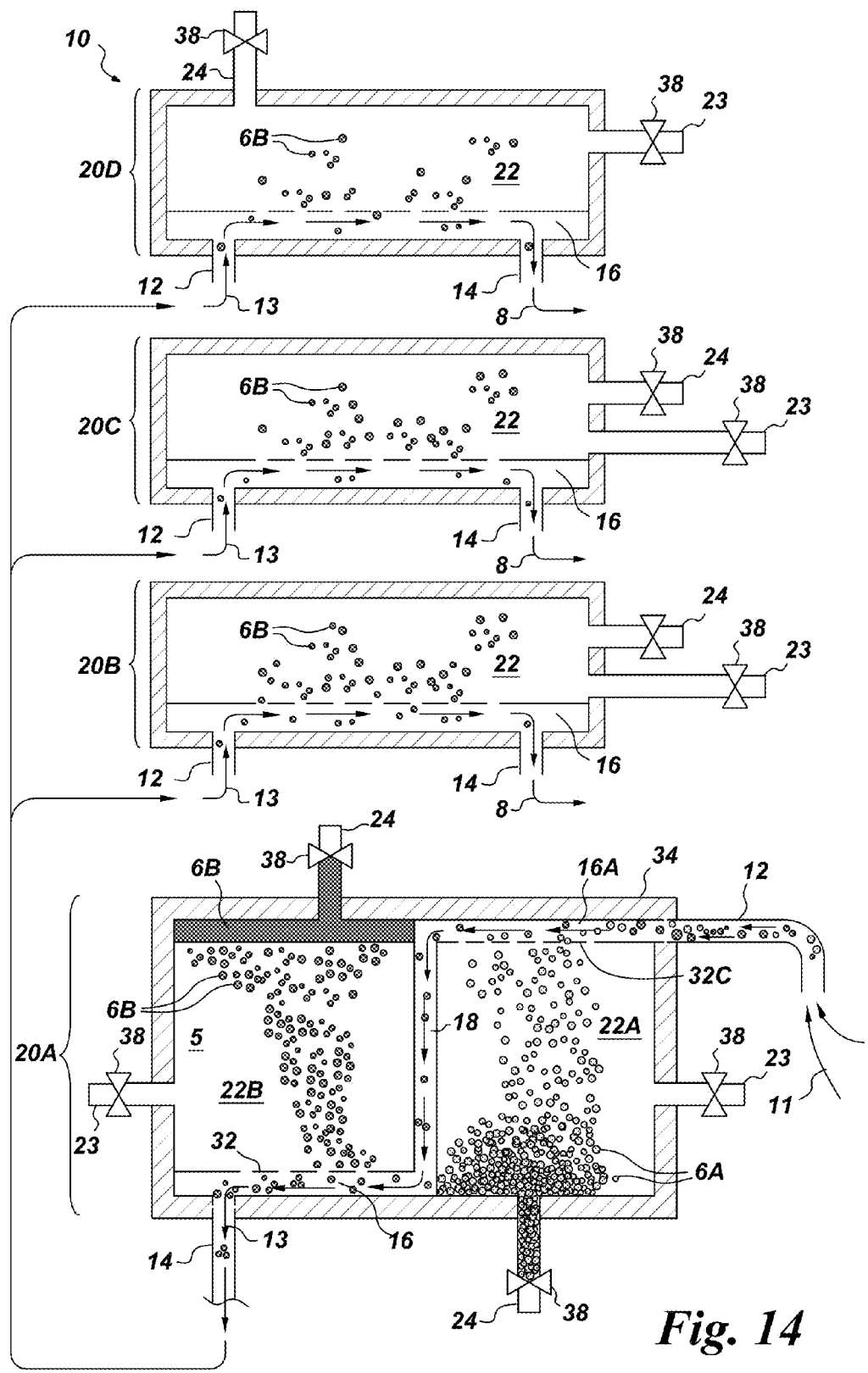

FIG. 14 further illustrates the separation system illustrated in FIG. 13 wherein the separation system comprises a plurality of microfluidic separation devices.

Figure 15:
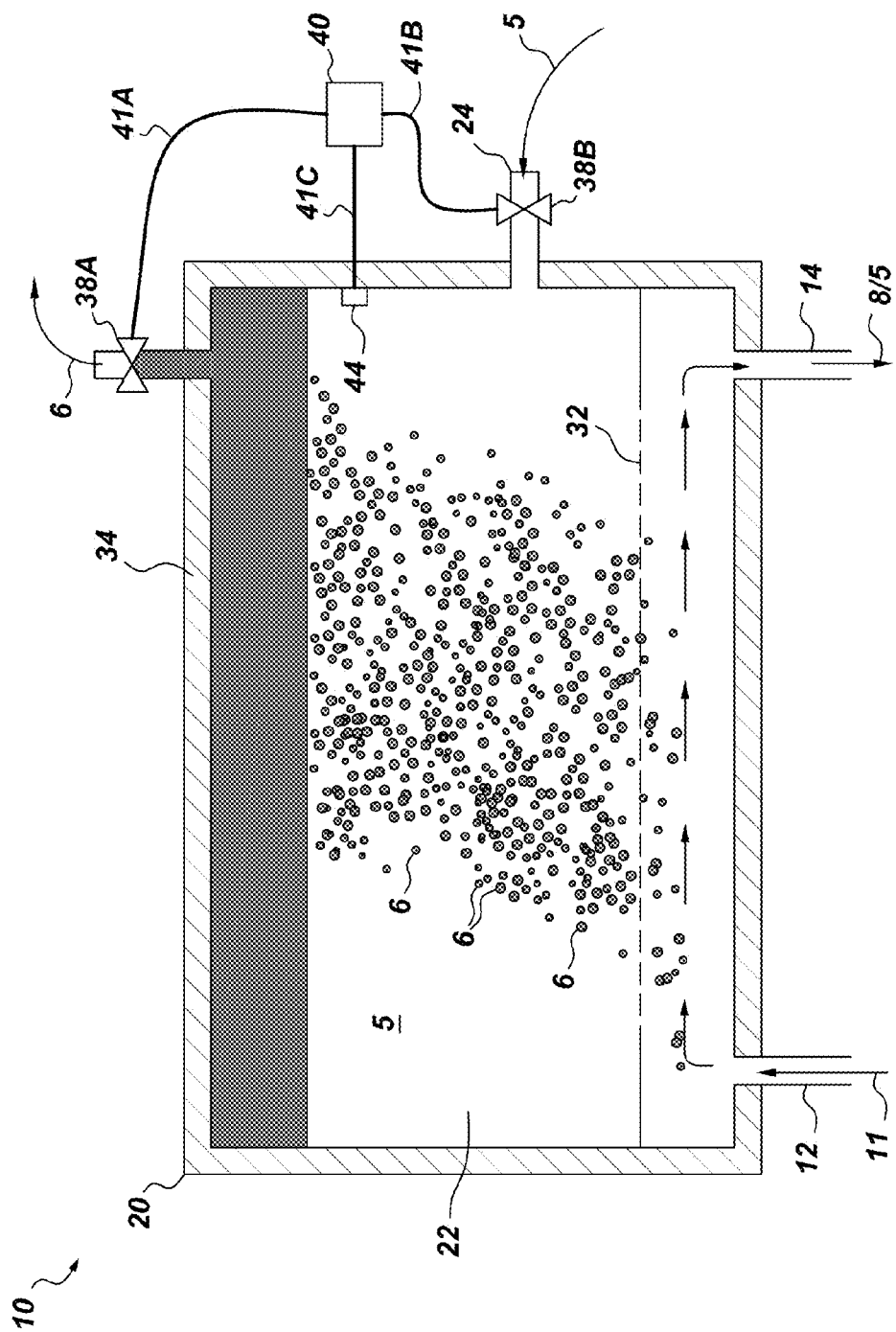

FIG. 15 illustrates a separation system provided by the present invention and a method for using such separation system.

Figure 16:
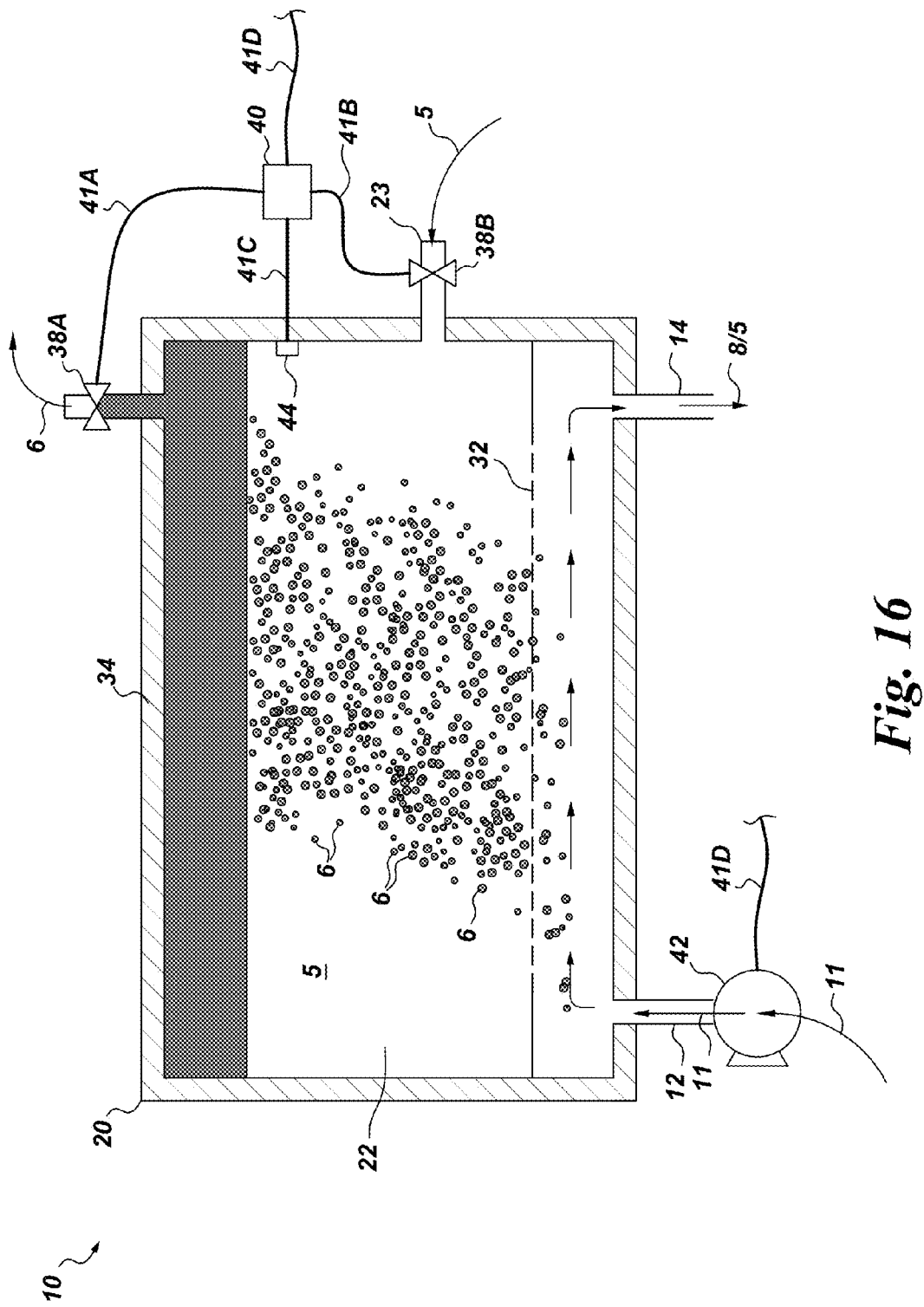

FIG. 16 illustrates a separation system provided by the present invention and a method for using such separation system.

DETAILED DESCRIPTION

Separation of particulates dispersed within a base fluid, for example separation of organic particulates (droplets) dispersed within an aqueous base fluid, may be effected using various embodiments of systems, devices and methods provided by the present invention. Embodiments of the system and its device components are illustrated in detail throughout this disclosure and comprise a fluid inlet for introducing the unprocessed fluid into the system, a fluid outlet for removing processed fluid from the system, and a separation region comprising a microchannel disposed between the fluid inlet and the fluid outlet, a microporous body defining at least a portion of the microchannel; and a collection chamber. The particulates dispersed in the base fluid (collectively "the unprocessed fluid") together with a portion of the base fluid itself under the influence of passive and/or active forces traverse the microporous body and are separated from the fluid flowing through the microchannel. The particulates and a portion of the base fluid are collected in a collection chamber disposed on an opposing side of the microporous body. Having traversed the microporous body, the particulates continue to migrate away from the microporous body under the influence of the passive and/or active forces. The base fluid is typically much less susceptible to the influence of the passive and/or active forces as compared to the particulates, and in various embodiments the base fluid entering the collection chamber may remain in relatively close proximity to the microporous body, and is subject to return to the microchannel by re-traversing the microporous surface. This dynamic of particulates and base fluid traversing, and base fluid re-traversing the microporous surface creates a flow regime within the collection chamber which has a lower flow rate relative to the flow rate of the fluid being processed through the microchannel. In various embodiments, the collection chamber is primed (i.e. partially or completely filled with a priming fluid (e.g. water, an organic liquid, or a mixture of water and an organic liquid) prior to the introduction of the unprocessed fluid into the microchannel. These concepts, useful in appreciating the systems, devices and methods provided by the present invention, are more fully developed below.

To more clearly and concisely describe the subject matter of the disclosed invention, the following definitions are provided for specific terms, which are used in the following description and the appended embodiments. Throughout the specification, exemplification of specific terms should be considered as non-limiting examples.

The terms "particulate" and "particle", and their plural referents "particulates" and "particles", are used interchangeably herein and are intended to have the same meaning, particle being treated as a synonym for particulate.

The singular forms "a", "an" and "the" include plural referents unless the context clearly dictates otherwise.

Approximating language, as used herein throughout the specification and disclosed embodiments, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Where necessary, ranges have been supplied, and those ranges are inclusive of all sub-ranges there between.

In one or more embodiments an external force causes the particulates and a portion of the base fluid to migrate through the microporous body. For example, the external force may be ambient gravity at times herein referred to as ambient gravitational forces. In an alternate embodiment, the external force may be a combination of the ambient gravitational forces present together with and an applied force field, such as an applied electric or magnetic field. In addition, the forces causing the particulates and base fluid to migrate across the microporous body may include one or more forces exerted by the fluid being processed through the microchannel.

In one embodiment, the microfluidic separation device is configured such that the ambient gravitational force acts upon the fluid being processed through the microchannel. Particulates having a density greater than the base fluid will tend to migrate downwardly, while particulates having a density lower than the density of the base fluid will tend to migrate upwardly in response to buoyancy forces. In either case, the system can be configured to allow capture of either or both of particles migrating downwardly and particles migrating upwardly in an appropriately configured collection chamber in fluid communication with the microchannel via the microporous body.

It is stressed that in various embodiments of the present invention, separation of particulates from the base fluid occurs as the fluid undergoing processing is flowing through the microchannel. Typically, the collection chamber and optionally the microchannel are filled with a priming fluid prior to initiating flow of the unprocessed fluid through the microchannel. As fluid flows through the device, a first flow regime characterized by a first flow rate is established in the microchannel and a second flow regime characterized by a second flow rate is established in the collection chamber, the second flow regime being characterized by a lower overall flow rate than that of the first flow regime.

As noted, the force which causes the particulates to traverse the microporous body may be an active force such as an applied electric field, a passive force such as the ambient gravitational field, or some combination thereof, for example in cases wherein the force of gravity augments the action of an externally applied electric field in inducing particulate movement.

The term microchannel is used to describe the channel into which the particulates dispersed in a base fluid are introduced and may be described as microfluidic since at least one of the dimensions of the microchannel is appropriately measured in microns (i.e., at least one of the primary dimensions of the microchannel; length, height, width, is 1000 microns or less). Typically, the microchannel has a length appropriately measured in units larger than microns, for example millimeters (mm), centimeters (cm) or meters (m). In one embodiment, the average height of the microchannel is between about 1 and about 1000 microns (μm). In an alternate embodiment, the average height of the microchannel is between about 10 and about 500 microns. In yet another embodiment, the average height of the microchannel is between about 20 and about 250 microns.

In one embodiment, the microchannel has a length $1$ between 5 mm and 25 cm. In another embodiment, the microchannel has a length $1$ between 10 mm and 10 cm. In yet another embodiment, the microchannel has a length $1$ between 10 mm and 25 mm. In yet still another embodiment, the microchannel has a length between 25 cm and 1 meter. The microchannel may of a regular shape (for example cylindrical) and be of uniform height h. Or, the microchannel may be of an irregular shape (for example a channel defined in part by an undulating wall) and be characterized by a plurality of heights h. Typically, however, the microchannel is rectangular in shape and is defined on three sides by walls enclosing the microchannel and on a fourth side by the microporous body.

As noted, the microchannel is disposed between a fluid inlet and a fluid outlet. Fluid enters the microfluidic separation device via the fluid inlet as unprocessed fluid, travels the length of the microchannel to the fluid outlet. During the passage of fluid from the inlet to the outlet, particulates migrate out of the microchannel and into the collection chamber under the influence of the fluid flow through the microchannel and one or more additional forces such as the ambient gravitational field, allied buoyancy forces, and applied force fields. The action within the microchannel converts the unprocessed fluid introduced at the fluid inlet into processed fluid emerging at the fluid outlet. In one embodiment, the fluid inlet is configured to receive a fluid comprising particulates dispersed within a base fluid, and to deliver the fluid to the microchannel under the influence of a system component, for example a vacuum line applied to the fluid outlet or a fluid pump upstream of the of the fluid inlet.

As noted, the microchannel is defined at least in part by the microporous body. In one embodiment, the microporous body constitutes one or more walls defining the microchannel. The microporous body may be a membrane or a solid body through which holes have been created. In one or more embodiments the microporous body comprises pores originating at a first surface of the microporous body and terminating at a second surface of the microporous body. In one or more embodiments, the microporous body is a film through which pores have been created. For example, pores traversing a film may be created by chemical etching techniques and/or laser ablative techniques. The term microporous is used herein because the pores have dimensions appropriately measured in microns (i.e., the average pore diameter is 1000 microns or less). In one embodiment, the pores have an average diameter between about 1 micron and about 500 microns. In an alternate embodiment, the pores have an average diameter between about 10 microns and about 250 microns. In yet another embodiment, the pores have an average diameter between about 20 microns and about 100 microns. In one embodiment, the porosity of the microporous body is between about 10 and about 75 percent. In an alternate embodiment, the porosity of the microporous body is between about 20 and about 65 percent. In yet another embodiment, the porosity of the microporous body is between about 30 and about 60 percent.

As noted, in one embodiment, the microporous body may be a microporous film such as a monofilament screen or mesh made from, for example, polyester, nylon, polypropylene, or a combination of such polymeric substances). Alternatively, the microporous body may be a chemically-etched KAPTON, titanium, or NiTinol film. In one embodiment, the microporous body is a laser etched organic film made from an organic polymeric material such as KAPTON.

As noted, the system comprises a collection chamber in fluid communication with the microchannel configured such that the collection chamber is situated on an opposing side of the microporous body. Typically, the collection chamber is configured such that the every pore of the microporous body enables direct fluid communication between the microchannel and the collection chamber. That portion of the microchannel-microporous body interface wherein this condition is met is at times herein referred to as the separation zone. The collection chamber is configured to collect particles which exit the microchannel during processing of the unprocessed fluid.

As noted, the system is configured such that a first fluid flow having a first flow rate through the microchannel together with the microporous body operationally generate a second fluid flow within the collection chamber as base fluid and particulates traverse the microporous body and enter the collection chamber, and as base fluid re-traverses the microporous body and re-enters the microchannel, the second fluid flow having a flow rate which is a fraction of the first flow rate.

The system may be configured, such that the time required for the particles to traverse the microporous body is less than the time required for the particles to transit the microchannel. The particle capture efficiency and/or volumetric throughput may be improved by either increasing the length $1$ or decreasing the height h of the microchannel. An increase in length $1$ of the microchannel increases the time available for the particles to interact with the microporous body. The efficiency with which particulates are removed from the fluid passing through the microchannel is at times herein referred to as "capture efficiency" and is believed to depend on a probability function, dependent on the average number of particles interacting with the pores during transit through the system and the probability of particle passage through a pore for each such interaction. The probability of particle passage through the pore for each interaction may depend on the ratio of particle size to pore size.

In some embodiments, the particle has an average diameter between 1 and 250 μm. In the case of particles which are not spherical, average diameter can be taken to mean largest particle dimension. As the microporous body comprises pores with an average diameter in a range of 1 to 500 μm, the particles that are smaller than the pore size may pass through the microporous body and enter the collection chamber. In cases in which the pores are not perfectly cylindrical in shape, the pore diameter can be taken to be the largest non-transverse dimension of the pore.

Figure 1:
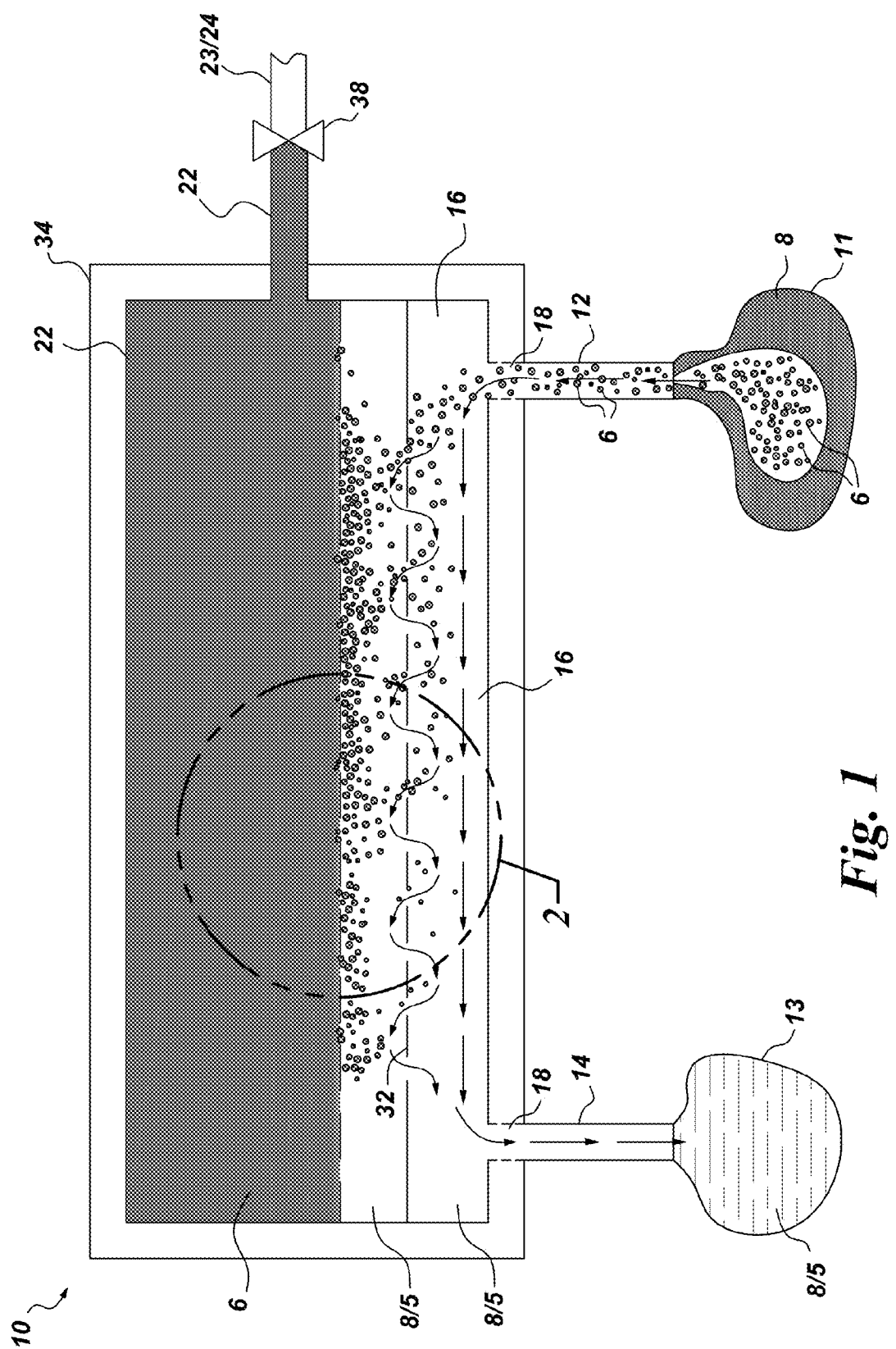
FIG. 1 illustrates a separation system provided by the present invention and a method for using such separation system.

Turning now to the figures, FIG. 1 illustrates a separation system 10 shown in cross section and method for using the same, the system comprising a fluid inlet 12, a fluid outlet 14 and a microchannel 16 disposed between the fluid inlet and fluid outlet. The fluid inlet 12 and fluid outlet are in fluid communication with microchannel 16 via channels 18. In the embodiment shown, the microchannel 16 is bounded on one side by microporous body 32. A collection chamber 22 is in fluid communication with the microchannel via microporous body 32. A first surface 32A (FIG. 2) of the microporous body 32 partially defines microchannel 16 and an opposing side 32B (FIG. 2) of the microporous body together with housing 34 defines collection chamber 22. In the embodiment shown, an unprocessed fluid 11 comprising particulates 6 of an organic liquid dispersed within an aqueous base fluid 8 is introduced into the system via fluid inlet 12. The unprocessed fluid may be impelled through the system using any suitable means, for example a fluid pump (See for example FIG. 8). In the embodiment shown, particulates 6 of the organic liquid are less dense than the base fluid 8 and rise in response to buoyant forces created by the ambient gravitational force field, while the denser base fluid 8 tends to remain within the microchannel and ultimately exits the system at fluid outlet 14 as processed fluid 13 depleted in particulates 6. Typically, the collection chamber 22 and microchannel 16 are filled with a primer fluid 5 prior to the introduction of unprocessed fluid 11 into the separation system. Particulates 6 traversing microporous body 32 tend to displace at least a portion of the primer fluid 5 from the collection chamber and into the microchannel where it mixes with the base fluid 8. Similarly, at least a portion of base fluid will traverse the microporous body together with particulates 6. In the embodiment shown, where a fluid is thought to comprise a mixture of base fluid 8 and primer fluid 5, the designation 8/5 or 5/8 is employed. It should be noted that the processed fluid 13, having been created, may be used as a primer fluid. Microporous body 32 is configured such that micropores 37 (See FIG. 2) defined by the microporous body allow particulates 6 of appropriate size to pass through the microporous body 32 and into collection chamber 22. In the embodiment shown, the captured particulates have nearly filled the collection chamber 22. Moreover, the particulates have coalesced into a single phase also designated by element number 6. In one or more embodiments, captured particulates 6 may be removed from the collection chamber via a collection chamber outlet 24. In the embodiment shown, collection chamber outlet may also serve as a collection chamber inlet through which additional primer fluid may be added after particulates have been removed from the collection chamber. In alternate embodiments, the collection chamber may comprise multiple collection chamber inlets and outlets.

Figure 2:
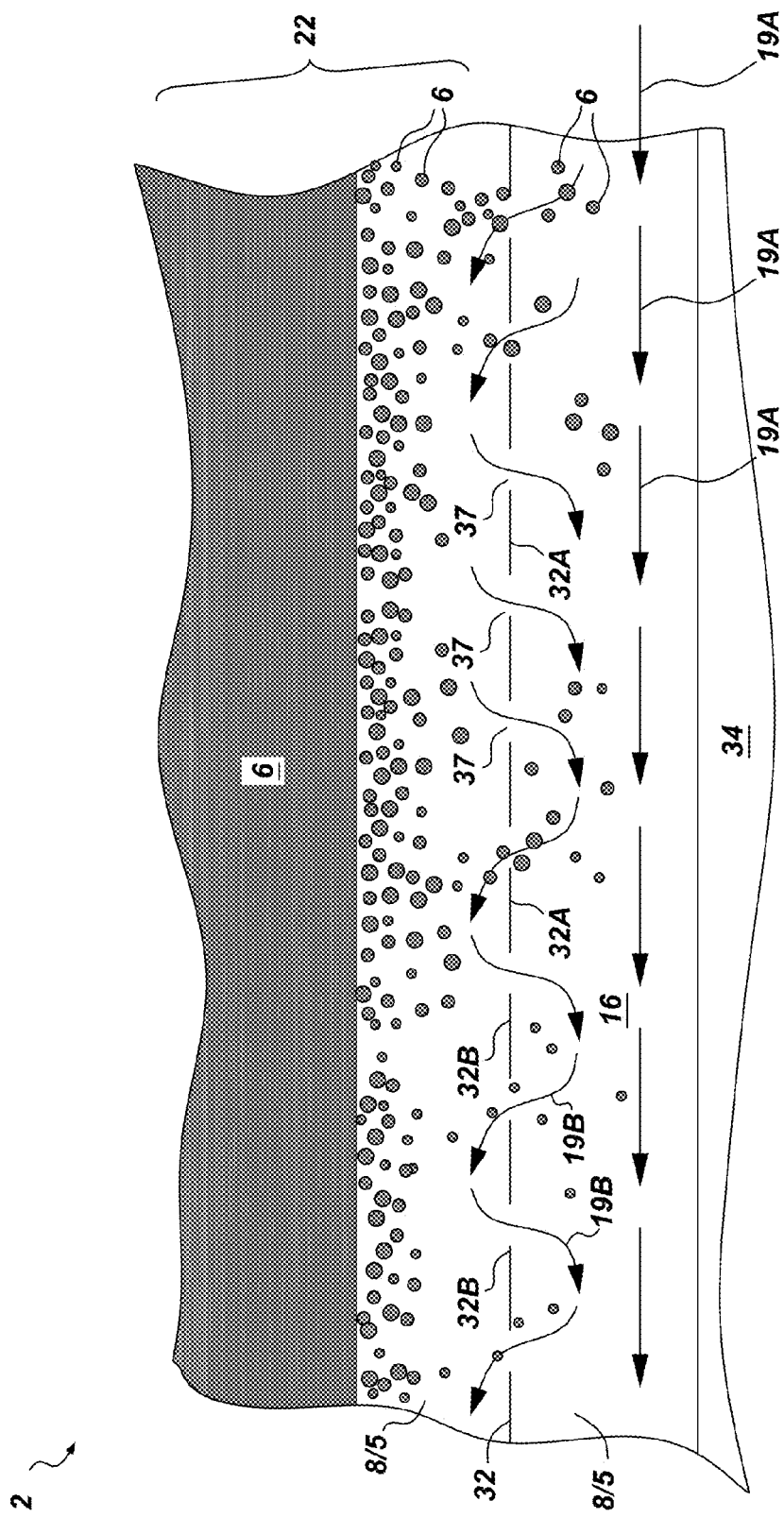
FIG. 2 is a close up view of the separation system illustrated in FIG. 1.

Referring to FIG. 2, the figure represents a magnified portion 2 of the separation system 10 shown in FIG. 1. In the embodiment shown, arrows 19A present in the microchannel 16 indicate the direction of flow of fluid through the microchannel at a first flow rate $v_1$ while the arrows 19B indicate second flow regime in which base fluid, primer fluid and particulates traverse and re-traverse the microporous body. This creates a second flow of fluid through collection chamber characterized by a second flow rate $v_2$, where the magnitude of $v_2$ is a fraction of the magnitude of $v_1$.

In one embodiment, the system 10 provided by the present invention is used to separate an unprocessed fluid 11 which is an oil in water emulsion comprising oil droplet particulates 6 dispersed in a water base fluid 8. The oil in water emulsion is introduced into the system via fluid inlet 12 as shown in FIG. 1. In the embodiment shown, oil droplets (the particulates) 6, are driven upwards by buoyancy through the microporous body and into the collection chamber 22 which is configured above the microporous body 32. As the oil droplets separate from the fluid flowing through the microchannel, oil is collected in the collection chamber and the processed fluid 13, water depleted in oil droplets, emerges at the system fluid outlet 14. In an alternate embodiment, water droplets may be separated from a heavier than water organic liquid using the systems and methods disclosed herein. For example, in one embodiment, a system 10 provided by the present invention is used to separate water droplets from a heavier than water base fluid comprising carbon tetrachloride. In such an embodiment and Referring to FIG. 1, element 6 represents water particulates dispersed in a heavier than water base fluid 8 comprising carbon tetrachloride. The water particulates traverse the microporous body 32 under the influence of buoyancy forces and coalesce in collection chamber 22. The processed fluid 13 comprising carbon tetrachloride is removed from the system via outlet 14. In an embodiment of the type just described a heavier than water primer fluid 5 may be employed. Those of ordinary skill in the art will appreciate that a system such as that shown in FIG. 1 may be appropriately valved on the inlet and outlet sides to prevent uncontrolled, gravity induced drainage of the contents of the collection chamber and microchannel. For example, fluid inlet 12 and fluid outlet 14 (FIG. 1) may be equipped with check valves having appropriate cracking pressures such that unprocessed fluid 11 enters and processed fluid 13 exits the system at essentially equal rates.

Referring to FIG. 3, the figure represents a separation system 10 configured to separate particulates 6 from an unprocessed fluid 11 comprising the particulates 6 dispersed in a base fluid 8. The particulates have a greater density than the base fluid and migrate downwardly in response to the ambient gravitational force field. In the embodiment shown, the base fluid 8 is an organic liquid and the particulates 6 represent a dispersed solid. The system comprises a fluid inlet 12 in fluid communication with a fluid outlet 14 via microchannel 16. The microchannel 16 is partially defined by a first surface 32A of microporous body 32. Microporous body 32 permits fluid communication between the microchannel and collection chamber 22. Collection chamber 22 is defined by an opposing side 32B of microporous body 32 and housing 34. In the embodiment shown, all of the particulates 6 have dimensions smaller than the micropores 37 defined by the microporous body and traverse the microporous body and enter the collection chamber where they settle under the influence of the ambient gravitational force field.

FIG. 4 illustrates an additional embodiment of the system 10 in operation, wherein the unprocessed fluid 11 comprising particulates 6 and a base fluid 8 comprises smaller particles 6 and larger particles 6. The unprocessed fluid enters the system through the inlet 12 and processed fluid processed fluid 13 exits the system through outlet 14. In the embodiment shown, larger particles 6 are larger than the diameter of the pores defined by the microporous body 32. The larger particles 6 cannot pass through microporous body to enter the collection chamber 22. Hence, larger particles 6 are retained in the processed fluid 13. Smaller particles 6 may pass through the microporous body 32 and are collected in the collection chamber 22. In the embodiment shown, the system enables particle separation based on particle size. In the embodiment shown, the microchannel has a rectangular shape having a length L and a height H.

FIG. 5 shows another embodiment of the system 10 in operation. In this embodiment, the unprocessed fluid comprises a plurality of particles 6 and agglomerated particles 7. The particles 6 and 7 are captured in segmented portions 22A and 22B of the collection chamber 22. Collection chamber portions 22A and 22B are separated by subdividing wall 22C. In the embodiment shown, the separation zone is divided into two portions, a first portion in which the pores of the microporous body are sized such that smaller particles 6 may pass through them and agglomerated particles 7 may not; and a second portion in which the pores of the microporous body are sized such that agglomerated particles 7 pass through them. In an alternate embodiment, the pores of the microporous body are sized such that both particles 6 and agglomerated particles 7 may pass through them, but the relative rates at which particles 6 and agglomerated particles 7 exit the microchannel and traverse the microporous body are such that a partitioning is achieved which is inverse to the partitioning idealized in FIG. 5. In such an alternate embodiment, particles 7 more rapidly exit the microchannel and traverse the microporous body and are collected in portion 22A of the segmented collection chamber shown in FIG. 5. Smaller particles 6 exit the microchannel and traverse the microporous body more slowly and are collected in portion 22B of the collection chamber shown in FIG. 5.

Another embodiment of the system 10 is shown in FIG. 6, wherein an unprocessed fluid is processed through the microchannel while being subjected to a combination of the ambient gravitational field and an additional applied force field. In the embodiment shown, particles 6 and particles 7 are constituted differently, particles 6 being susceptible to being set in motion under the influence of a magnetic field and particles 7 not being susceptible thereto. In the embodiment shown, a magnetic field is applied across the collection chamber 22, the microporous body 32 and the microchannel 16 by means of an electromagnet 36 and its allied controller/power source 40. Magnetically susceptible particles 6 are drawn across microporous body 32 under the influence of a combination of both the ambient gravitational field and the applied magnetic field created by electromagnet 36.

Still referring to FIG. 6, in an alternate embodiment, the applied magnetic field is used to overcome the ambient gravitational field in achieving particle separation. For example, wherein the system 10 shown in FIG. 6 is inverted such that only particles tending to migrate upwardly under the influence of the ambient gravitational field would be susceptible to traversing the microporous body 32 and capture by the collection chamber 22. In such an example, particles 7 are more dense than the base fluid, and as a result are not susceptible to migrating upwardly under the influence of the ambient gravitational filed. Particles 7 can be forced to migrate upwardly using an applied magnetic field, provided the particles 7 are magnetically susceptible. In this example, particles 7 are magnetically susceptible while particles 6 are not magnetically susceptible, and particles 6 being more dense than the base fluid are not susceptible to migrating upwardly under the influence of the ambient gravitational field. Under such circumstances, particles 7 can be forced to migrate upwardly and be captured in and retained within the collection chamber 22 under the influence of a magnetic field applied by electromagnet 36, and are thereby separated from particles 6.

Figure 7:
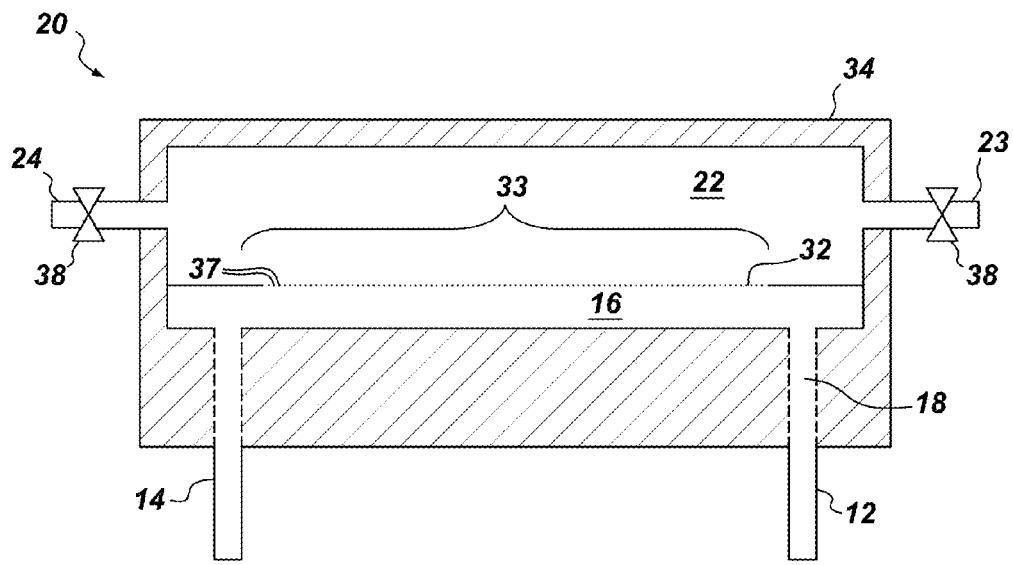
FIG. 7 illustrates a microfluidic separation device provided by the present invention.

Referring to FIG. 7, the figure represents a device 20, at times herein referred to as a microfluidic separation device, suitable for separating oil dispersed in water. In the embodiment shown, the device comprises a fluid inlet 12; a fluid outlet 14; a microchannel 16 disposed between the fluid inlet and fluid outlet; a microporous body 32 defining at least a portion of the microchannel; and a collection chamber 22 on an opposing side of the microporous body, the collection chamber being in fluid communication with microchannel 16 via pores 37 of the microporous body 32. In the embodiment shown, the microporous body and the microchannel define a separation zone 33. The collection chamber 22 is equipped with collection chamber inlet 23 and collection chamber outlet 24 and valves 38.

Figure 8:
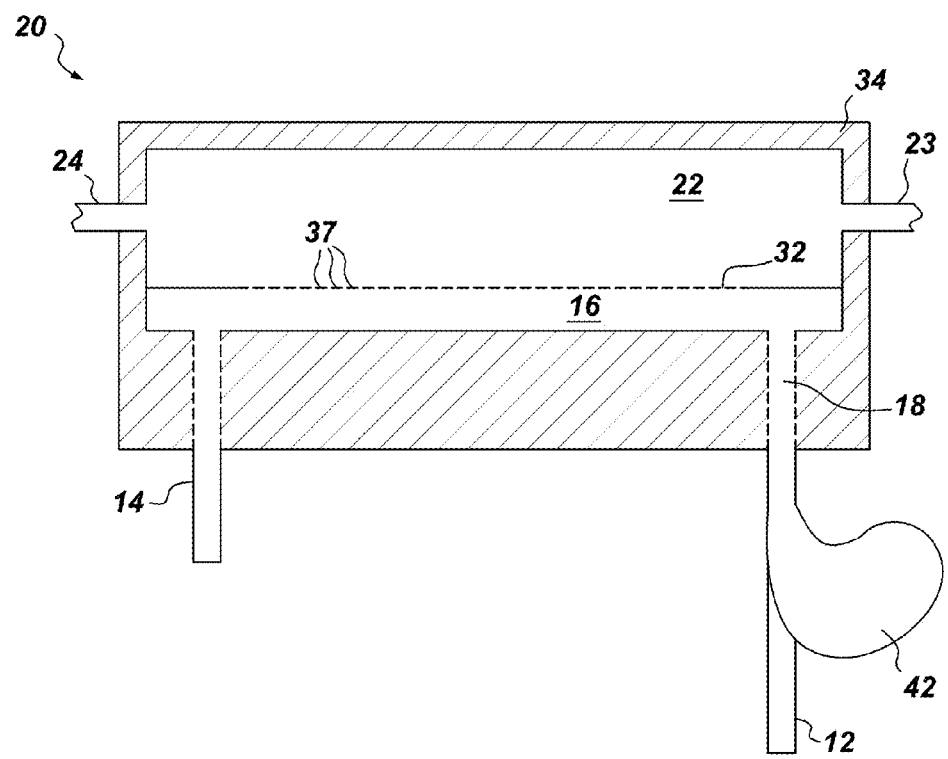
FIG. 8 illustrates a microfluidic separation device provided by the present invention.

Referring to FIG. 8, the figure represents a microfluidic separation device 20 configured essentially as in FIG. 7 but further comprising a fluid driver 42. In one embodiment, the fluid driver is a pump capable of pumping oil-water emulsions.

Figure 9:
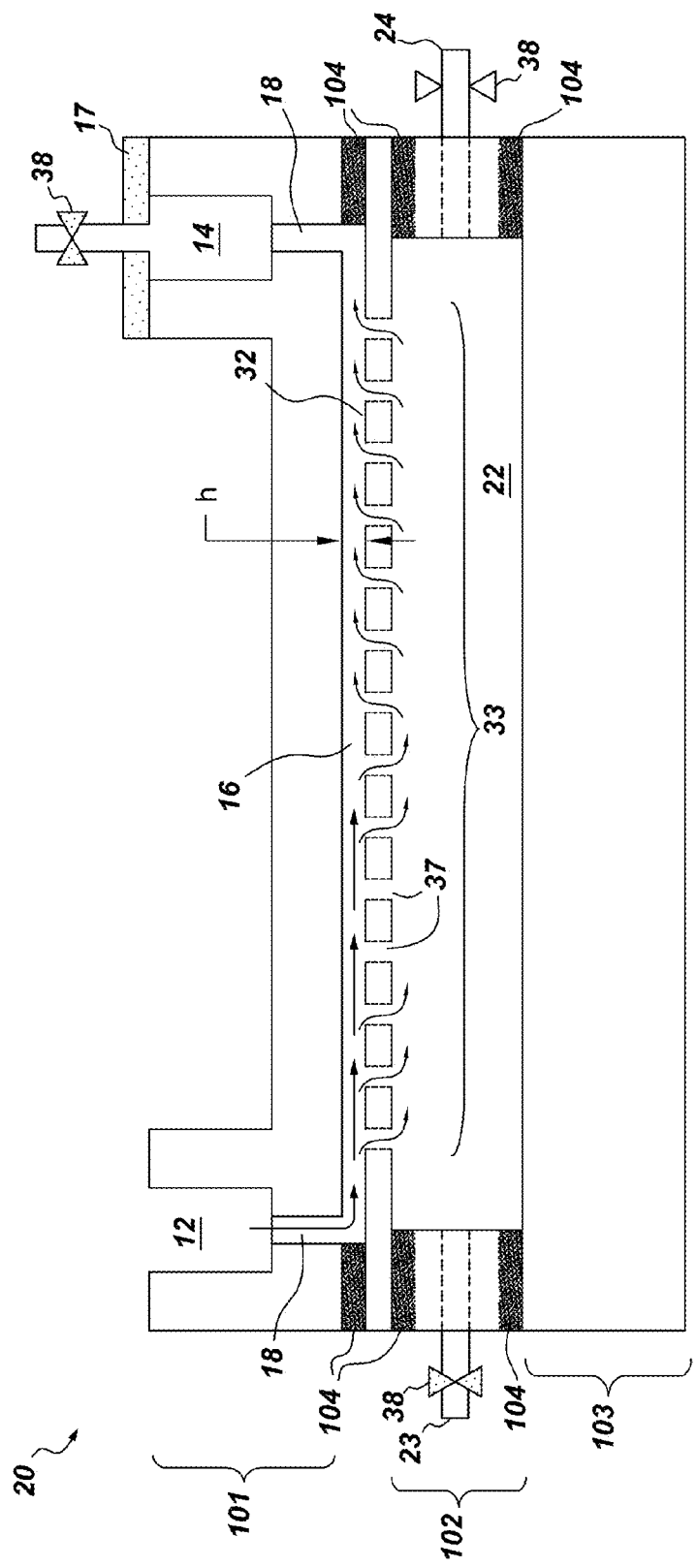
FIG. 9 illustrates a microfluidic separation device provided by the present invention.
Figure 10:
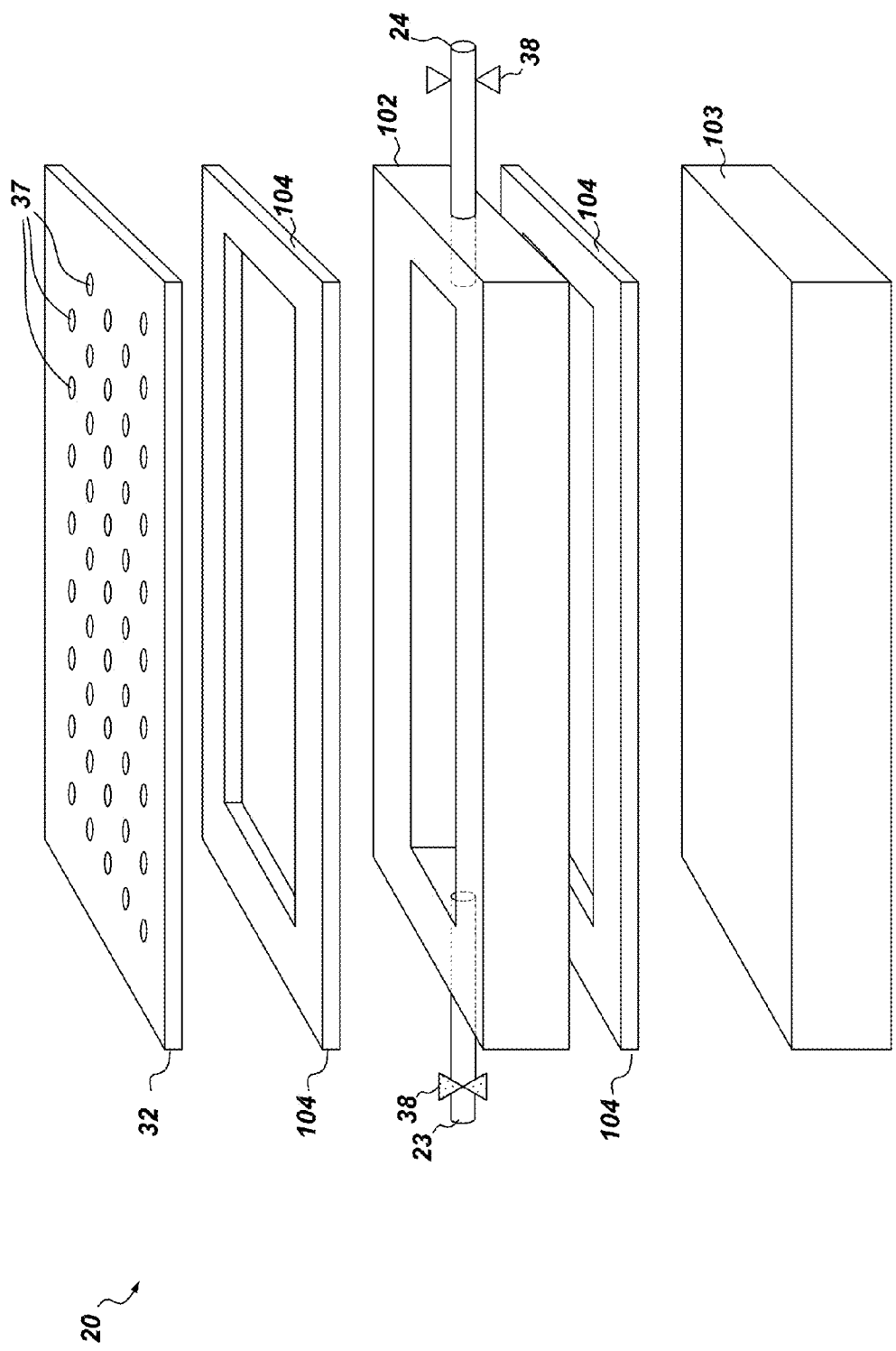
FIG. 10 illustrates a portion of a microfluidic separation device provided by the present invention shown in an exploded view.
Figure 11:
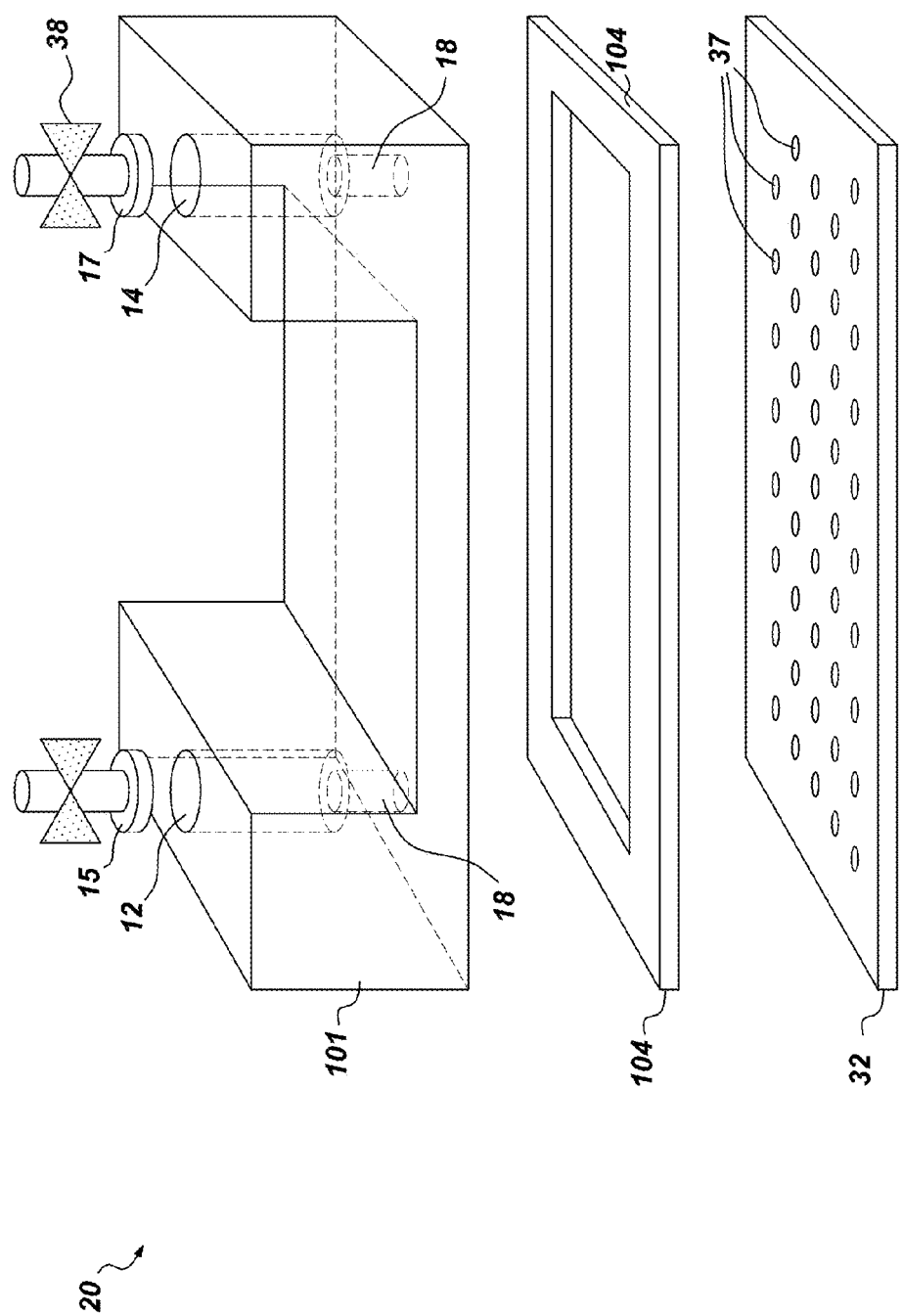
FIG. 11 illustrates a portion of a microfluidic separation device provided by the present invention shown in an exploded view.

Referring to FIG. 9, the figure represents a microfluidic separation device 20 and a method for its assembly. The microfluidic separation device may be used according to one or more embodiments of the present invention. Details of the assembly of the embodiment shown in FIGS. 9-11 are provided in the Experimental Part of this disclosure.

Figure 12:
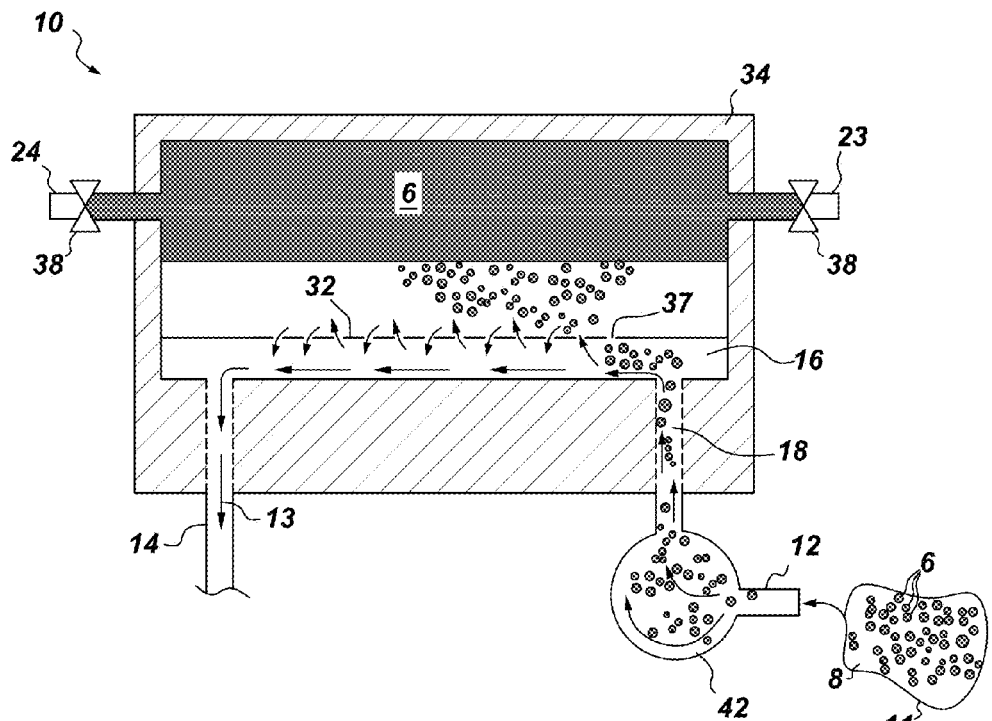
FIG. 12 illustrates a separation system provided by the present invention and a method for using such separation system.

Referring to FIG. 12, the figure represents a system 10 provided by the present invention, the system being configured to receive an unprocessed fluid 11 comprising particulates 6 dispersed in a base fluid 8 from an unprocessed fluid source, for example stream of a lighter than water organic fluid dispersed as particulates 6 in an aqueous base fluid 11, as might be produced in a chemical process step in a manufacturing operation. The use of the system 10 enables the separation and recovery of a purified aqueous processed fluid stream 13 and the organic fluid.

Referring to FIG. 13, the figure represents a system provided by the present invention deployed in an oil production application. In the embodiment shown, production fluid generated from a producing hydrocarbon reservoir 50 undergoing waterflood enhanced oil recovery treatment, is separated into a recovered hydrocarbon stream 6 (shown as emerging from the top of system 10) and an aqueous processed fluid stream 13/8. Thus, water 8 is introduced into the reservoir through injection well 62 and permeates the reservoir and drives both water 8 and a liquid hydrocarbon 6 into production well 61 as water dispersed in the liquid hydrocarbon 8/6, liquid hydrocarbon dispersed in water 6/8 as well as separate water and hydrocarbon phases. A complex multiphase production fluid is impelled by an electric submersible pump 52 to a surface separation installation comprising system 10 and linked to the production well 61 by surface conduit 56. At least a portion of the production fluid constitutes an unprocessed fluid 11 comprising a mixture of hydrocarbon droplets 6 dispersed in an aqueous base fluid 8. In addition, at least a portion of the production fluid constitutes an unprocessed fluid 11 comprising a mixture of aqueous droplets 8 dispersed in a hydrocarbon base fluid 6. The water initially injected into the reservoir typically encounters brine and/or water soluble salts in the reservoir. As a result, the water phases in the production fluid may in be in the form of a relatively complex brine fluid when introduced into separation system 10. Processed fluid 13/8 may then be recirculated into the reservoir via conduit 58, injection unit 60 and injection well 62.

Referring to FIG. 14, the figure represents a separation system 10 provided by the present invention comprising a plurality of microfluidic separation devices 20A-20D. As will be appreciated by those of ordinary skill in the art system 10 may be particularly useful in oil production applications such as that featured in FIG. 13. In the embodiment shown, an unprocessed fluid 11 is introduced into a first microfluidic separation device 20A comprising a pair of collection chambers 22A and 22B. Unprocessed fluid 11 comprising solid particulates 6A and organic liquid particulates 6B dispersed in an aqueous base fluid are introduced into channel 16A which is separated from collection chamber 22A by porous body 32C. Channel 16A may be a microchannel or a larger channel none of the dimensions of which are appropriately measured in microns (i.e., no dimension of the channel is 1000 microns or less). Similarly, porous body 32C may be a microporous body (i.e., the average pore diameter is 1000 microns or less) or a porous body defining larger pores the dimensions of which are not appropriately measured in microns (i.e., the average pore diameter is more than 1000 microns). As the fluid being processed passes through channel 16A, particulates 6A being heavier than the base fluid traverse the porous body 32A under the influence of the ambient gravitational field and are captured in collection chamber 22A. Particulates 6A may be removed from collection chamber 22A via valved collection chamber outlet 24. Collection chamber inlet 23 may be used for the addition of make-up primer fluid to collection chamber 22A during the removal of particulates 6A. Following removal of particulates 6A by passage through channel 16A, the resultant mixture of organic liquid particulates 6B dispersed in an aqueous base fluid is introduced into microchannel 16 of device 20A via connecting channel 18. Particulates 6B, being less dense than the base fluid, traverse microporous body 32 under the influence of buoyancy forces and are collected in collection chamber 22B. Processed fluid 13 comprising residual organic liquid particulates 6B, aqueous base fluid, and primer fluid 5 is then transferred (e.g., impelled by a pump) to three microfluidic separation devices 20B-20D arranged in parallel which capture residual organic liquid particulates 6B and produce purified aqueous fluid 8.

Referring to FIG. 15, the figure represents a system 10 comprising a microfluidic separation device 20 provided by the present invention which may be used to separate oil-water mixtures. In the embodiment shown, the collection chamber 22 is equipped with valved collection chamber inlet 23 and collection chamber outlet 24. Valves 38A and 38B are activated by controller 40 which in response to sensor 44 may open and/or close valves 38A and 38B, for example to remove coalesced oil 6 from the collection chamber while simultaneously introducing make-up primer fluid 5 into the collection chamber respectively. Controller 40 is linked to valves 38A, 38B and sensor 44 by connections 41A, 41B and 41C respectively. Remotely controlled valves such as valves 38A and 38B, and sensors such as sensor 44 are either articles of commerce or are known to those of ordinary skill in the art.

Referring to FIG. 16, the figure represents a system 10 comprising a microfluidic separation device 20 that may be used according to one or more embodiments of the present invention. In the embodiment shown, device 20 is configured as in FIG. 15 and further comprises a pump 42 configured to introduce an unprocessed fluid into microchannel 16 via fluid inlet 12. Pump 42 is linked to controller 40 by connection 41D and is controlled thereby. In one embodiment, controller 40 directs that the rate of flow of unprocessed fluid into microchannel 16 be changed in response to a change in the disposition of either or both of valves 38A and 38B. For example, controller 40 may direct pump 42 to reduce or interrupt the flow of unprocessed fluid 11 into microchannel 16 while valves 38A and 38B are open to remove coalesced oil 6 from the collection chamber while simultaneously introducing make-up primer fluid 5 into the collection chamber respectively.

The systems, devices and methods provided by the present invention have been are shown experimentally herein to be applicable to the separation of heavier than water solid particulates from an aqueous base fluid (See Examples 1-4) as well as the separation of complex oil-water emulsions (Example 5). Full experimental details are provided in the Experimental Part which follows.

EXPERIMENTAL PART

Device Rapid Prototyping

A microfluidic separation device housing was created using a commercially available rapid prototyping instrument and an ABS-like photopolymer (DSM Somos WaterShed XC 11122). The microfluidic separation device was assembled from three parts created on the rapid prototyping instrument together with a porous KAPTON film which served as the microporous body, and a set of pressure sensitive adhesive films which joined the parts together and served to create the microchannel. Useful reference may be made to FIGS. 9-11 to better understand the fabrication of the microfluidic separation device.

The first part 101 (FIG. 11) comprised a fluid inlet 12 and fluid outlet 14 with channels 18 linking each to microchannel 16 (FIG. 19). Fluid inlet 12 and fluid outlet 14 are equipped with a device inlet fitting 15 and device outlet fitting 17 respectively. The second part 102 (FIG. 10) defined the collection chamber 22 (FIG. 9). A third part 103 (FIG. 10) formed a wall of the collection chamber. A 50 micron (μm) thick pressure sensitive adhesive 104 (FIG. 11) was used to define the microchannel having dimensions 50 millimeters by 10 millimeters by 50 microns and comprised features cut out using a cutter/plotter (Graphtec Craft Robo ProS). The adhesive film 104 also served to fix the microporous body 32 (FIGS. 9-11) (the porous KAPTON film) to the first part 101. Additional cut adhesive films 104 were used to fix the second part 102 to the microporous body 32 and the third part 103 (FIG. 10). In the embodiment shown, microporous body 32 comprises pores 37.

Two different types of microporous bodies were used in the devices practice of the invention. As mentioned, the first type of microporous body was formed from a KAPTON sheet with laser-machined pore arrays having average pore diameter of about 21.7 microns with a 50 micron center-to-center pore spacing. The second type of microporous body employed was a medical grade polyamide woven mesh having 40 micron pores and 40% porosity (SEFAR MEDIFAB, 07-40/40).

The collection chamber 22 defined by second part 102 had dimensions of 40 millimeters by 10 millimeters by 2 millimeters, resulting in a 750 microliter (μL) holding volume.

Device Operation

The microfluidic separation device was equipped with two ports 23 and 24 (FIGS. 9-10) which enabled the device to be primed easily before use. Typically, the device was primed by introducing deionized water through one of the two ports 23 and 24 and completely filling both the collection chamber 22 and the microchannel 16 before use. Alternatively, the device could be primed by flowing deionized water from the fluid inlet and into the microchannel and collection chamber. Typically, the priming liquid could be introduced into the microfluidic separation device without introducing air bubbles.

Water Purification

Materials

TAN clay as obtained from GE Water and Process Technologies and used as received. Kaolin clay was purchased from Sigma-Aldrich and used as received. Water treatment products PC2700, CE1169 and GS-550 were purchased from GE Water and Process Technologies and made into dosing solutions as per the vendor instructions. Fulcat-200, Fulcat-400, Fulcat-400, and Fulcat-436 were purchased from Southern Clay Products and used as received. Field sourced produced water was obtained from one or more producing natural gas wells. Particle size distributions were measured by image analysis of optical images captured using a confocal microscope at 200× magnification. Effluent turbidity was measured using a HACH Ratio/XR Benchtop Turbidimeter.

Device Fabrication

A 160 mm×30 mm microporous body comprising 100 µm pores was prepared by laser-etching a KAPTON film. The pores were spaced 255 µm on center in a grid pattern yielding more than one million pores across the porous portion of the microporous body. Pore size and spacing were measured by image analysis of optical microscopy images. The porous portion of the KAPTON film constituting the separation zone was about 3200 mm$^2$. A microfluidic separation device was prepared from polycarbonate sheets and the porous KAPTON film. An upper sheet of ¼ inch thick polycarbonate equipped with a threaded fluid inlet and a threaded fluid outlet was joined to the porous KAPTON film using two layers of pressure sensitive adhesive cut to the dimensions of the upper sheet of polycarbonate and bounding the microchannel and each layer having a thickness of 50 microns to form a first device subassembly. The total height of the microchannel was about 100 microns. In some instances additional layers of the pressure sensitive adhesive were used to increase the height of the microchannel (See Example 1 below). A second polycarbonate sheet was provided and was used to form the base of the microfluidic separation device. A collection chamber was milled to a depth of 2 mm in the second sheet of polycarbonate. Threaded inlet and outlet ports were created in the second sheet of polycarbonate to permit an additional mode of fluid communication with the collection chamber. The second sheet of polycarbonate was then joined to the first subassembly with an appropriately sized 50 micron thick pressure sensitive adhesive such that the collection chamber was aligned with the porous part of the KAPTON film. The fluid inlet, the fluid outlet and the ports communicating with collection chamber were fitted with barbed hose fittings appropriate for ⅛-¼ inch peristaltic pump grade rubber tubing. A peristaltic pump was used to pump fluids comprising particulates dispersed in a base fluid through the device at flow rates ranging from about 1 to about 500 milliliters per minute. The peristaltic pump was also used to introduce priming fluid into the device.

Device Operation

Unless otherwise specified, the device seas oriented level with the plane of a benchtop with the collection chamber positioned below the microchannel. The collection chamber and microchannel of the device were primed with deionized water prior to introduction of the particulate-containing base fluid. Particulates traversed the macroporous body and separated from the base fluid under the influence of gravity acting as the external force field. During operation, the fluid comprising particulates dispersed within a base fluid was introduced through the fluid inlet into the microchannel and left the device via the fluid outlet, while the inlet and outlet ports of the collection chamber remained closed. The device could be operated in both single pass and multi-pass (recirculating) modes. In single pass experiments the processed fluid was collected in a graduated cylinder and run times were recorded using a stopwatch in order to estimate flow rates through the device.

Example 1: Separation of Clay Particulates from an Aqueous Base Fluid

A TSS (Total Suspended Solids; tan clay) calibration sample having a concentration of 2000 milligrams per liter dispersed in deionized water was prepared and tested. The size of the clay particles was between about 1 and about 47 µm. The microfluidic separation device used was that described above with the exception that the height of the microchannel was increased to about 200 microns using additional pressure sensitive adhesive layers in order to facilitate passage of the larger particulates through the microchannel. Turbidities of the unprocessed and processed fluids were measured with a commercial nephelometer, and results were recorded in nephelometric turbidity units (NTU).

The initial turbidity of the calibration sample was 1040 NTU. The calibration sample was introduced through the fluid inlet and through the microchannel flow rates between about 5 and about 20 milliliters per minute and yielded processed fluids having turbidities between 85 and 460 NTU, illustrating the effectiveness of the microfluidic separation device provided by the present invention at removing particulates from water.

Example 2: Separation of Particles from Clay Suspensions

Clay suspensions were prepared at 500 mg/l, concentrations in deionized water for each of Fulcat-200 Fulcat-400, and Fulcat-436 clays. Particle size distributions were 1 to 50 µm, 1 to 33 µm, and 1 to 33 µm for the Fulcat-200, Fulcat-400, and Fulcat-436 clays, respectively. Initial turbidities were 90, 100, and 40 NTU for the Fulcat-200, Fulcat-400, and Fulcat-436 clays, respectively. Each suspension was pumped through the microchannel of the system at feed rates between 20 and 75 mL/min yielding effluent with turbidities between 6 and 60 NTU. Each of the clay suspensions from this example were dosed with 0.5 mg/L of the flocculant CE1169. Each dosed suspension was pumped through the microchannel of the system at feed rates between 20 and 75 mL/min yielding effluent with turbidities between <1 and 20 NTU.

Example 3: Separation of Kaolin Clay Particulates from Brine

A 1000 mg/L clay suspension was prepared of a 1:1/TAN: kaolin clay mixture (weight:weight; in brine having a salt concentration of 102.5 grams per liter. The suspension was then treated with 250 mg/mL of organics that simulate the organics found in produced water from natural gas exploration. The Kaolin particle size distribution was between 1 and 10 pun. The original suspension turbidity was >1500 NTU. The clay suspension was dosed with 25 mg/mL of the coagulant PC2700 and 0.3 mg/L of the flocculant CE-1169.

A 1 L sample of the suspension was pumped through the microchannel of the system at 10 mL/min yielding effluent with turbidities between 5 and 10 NTU. The fluid collected in the collection chamber (about 6 mL) was removed and the collection chamber was rinsed with about 12 mL of the processed brine removed from the fluid outlet. Thus, the efficiency of brine recovery was about 98% ((1000 mL-6 mL-12 mL/1000 mL)×100=98%).

Example 4: Separation of Particulates from Field-Sourced Water

A blended sample of field-sourced water was prepared from water samples obtained from the Polley natural gas facility in Texas, USA and the Utica natural gas facility in Ohio, USA. The 80:20/Polley:Utica (volume:volume) blend had an initial turbidity of 950 NM. The blend was pumped through the microfluidic separation device described above at feed rates between 20 and 75 mL/min yielding processed fluid stream having turbidity between 78 and 340 NTU depending on the feed rate.

The effect of flocculant was also tested. Thus, the blended field sourced water from this experiment was dosed with 0.5 mg/L of the flocculant CE1169. The dosed suspension was pumped through the microchannel of the device at feed rates between 20 and 75 mL/min. yielding effluent with turbidities between 17 and 95 NTU.

Separation of Oil in Water Emulsions

Example 5

A model oil solution consisting of a one to one mixture of dodecane and hexadecane and containing 1% TWEEN® 20 was prepared. A 10 g aliquot of the model oil solution was blended with 1 L of deionized water in a WARING blender for 0.5 minutes yielding a stable oil in water emulsion with an initial turbidity of 995 NTU. The device used in the water purification examples above (Examples 1-4) was mounted parallel to the bench top, but with the collection chamber positioned above the microchannel to allow buoyancy forces to induce the particulates the oil droplets) dispersed within the water to migrate upwardly through the microporous body (the porous KAPTON film). The emulsion was pumped through the microchannel at 10 mL/min yielding a processed fluid effluent with a turbidity of 210 NTU. The collection chamber contained a visibly concentrated emulsion.

The effect of a de-emulsifier in combination with the use of the microfluidic separation device was also investigated. Thus, the starting oil in water emulsion prepared above was dosed with 1 mg/L of an emulsion breaker, GS-55G. The dosed emulsion was pumped through the microchannel of the system at 10 mL/min yielding a processed fluid effluent with a turbidity of 155 NTU. The collection chamber contained a visibly concentrated emulsion. The processed fluid effluent was then recirculated through the microfluidic separation device at a flow rate of 10 milliliters per minute. After 60 minutes of recirculation the collection chamber was observed to contain a coalesced model oil layer and the turbidity of the processed fluid effluent was 120 NM.

While only certain features of the invention have been illustrated and described herein, many modifications and changes will occur to those skilled in the art. It is, therefore, to be understood that the appended embodiments are intended to cover all such modifications and changes as fall within the scope of the invention.

What is claimed is:

1. A system for separating particulates dispersed within a base fluid, the system comprising:
   a fluid inlet;
   a fluid outlet;
   a microchannel disposed between the fluid inlet and fluid outlet;
   a microporous body defining at least a portion of the microchannel; and
   a collection chamber on an opposing side of the microporous body;
   the system being configured such that the particulates and a portion of the base fluid traverse the microporous body under the influence of an ambient gravitational field and are collected in the collection chamber;
   and such that a first fluid flow having a first flow rate through the microchannel together with the microporous body operationally generate a second fluid flow within the collection chamber as base fluid and particulates traverse the microporous body and enter the collection chamber, and as base fluid re-traverses the microporous body and re-enters the microchannel, the second fluid flow having a flow rate which is a fraction of the first flow rate;
   and such that at least one of the particulates and the base fluid comprises an organic liquid.

2. The system of claim 1, wherein the organic liquid comprises petroleum.

3. The system of claim 1, wherein the base fluid is water.

4. The system of claim 1, wherein the base fluid is an organic liquid.

5. The system of claim 1, wherein the particulates comprise solid matter.

6. The system of claim 1, wherein the collection chamber and the microchannel are filled with a primer fluid prior to the particulates and a portion of the base fluid traversing the microporous body under the influence of the ambient gravitational field.

7. The system of claim 1, wherein the external force field comprises an applied force field selected from among an applied magnetic field and an applied electric field.

8. The system of claim 1, wherein the microchannel has an average height between about 1 micron and about 1000 microns (μm).

9. The system of claim 1, wherein the microchannel has a length 1 between about 25 centimeters and about 1 meter.

10. The system of claim 1, wherein the particulates have an average largest dimension between about 1 micron and about 250 microns.

11. The system of claim 1, wherein the microporous body comprises pores with an average diameter between about 10 microns and about 500 microns.

12. The system of claim 1, wherein the microporous body has porosity between about 10 percent and about 75 percent.

13. The system of claim 1, further comprising one or more of a collection chamber fluid inlet and a collection chamber fluid outlet.

14. The system of claim 1, further comprising one or more controllers for controlling an applied external force field.

15. The system of claim 1, further comprising a fluid driver to induce a flow of particulates dispersed within a base fluid through the microchannel to afford a processed fluid enriched depleted in particulates.

16. The system of claim 1, further comprising one or more controllers to control the first fluid flow.

17. A system for separating organic liquid particulates dispersed in an aqueous base fluid, the system comprising:
   a fluid inlet;
   a fluid outlet;

a microchannel disposed between the fluid inlet and fluid outlet;

a microporous body defining at least a portion of the microchannel; and a collection chamber on an opposing side of the microporous body;

the system being configured such that the particulates and a portion of the aqueous base fluid traverse the microporous body under the influence of an ambient gravitational field and are collected in the collection chamber;

and such a first fluid flow having a first flow rate through the microchannel together with the microporous body operationally generate a second fluid flow within the collection chamber as aqueous base fluid and particulates traverse the microporous body and enter the collection chamber, and as the aqueous base fluid re-traverses the microporous body and re-enters the microchannel, the second fluid flow having a flow rate which is a fraction of the first flow rate.

18. The system of claim 17, wherein the organic liquid particulates comprise a solvent.

19. The system of claim 18, wherein the organic liquid is petroleum.

20. A system for separating particulates dispersed in an organic base fluid, the system comprising:
 a fluid inlet;
 a fluid outlet;
 a microchannel disposed between the fluid inlet and fluid outlet;
 a microporous body defining at least a portion of the microchannel; and
 a collection chamber on an opposing side of the microporous body;
the system being configured such that the particulates and a portion of the hydrocarbon base fluid traverse the microporous body under the influence of an ambient gravitational field and are collected in the collection chamber;
and such that a first fluid flow having a first flow rate through the microchannel together with the microporous body operationally generate a second fluid flow within the collection chamber as base fluid and particulates traverse the microporous body and enter the collection chamber, and as base fluid re-traverses the microporous body and re-enters the microchannel, the second fluid flow having a flow rate which is a fraction of the first flow rate.

21. The system of claim 20, wherein the particulates comprise water.

22. The system of claim 20, wherein the particulates comprise solid matter.

23. A method for separating particulates dispersed within a base fluid, the method comprising:
 (a) providing a separation device comprising:
  (i) a fluid inlet;
  (ii) a fluid outlet;
  (iii) a microchannel disposed between the fluid inlet and the fluid outlet;
  (iv) a microporous body defining at least a portion of the microchannel; and
  (v) a collection chamber on an opposing side of the microporous body;
 (c) introducing via the fluid inlet a stream of unprocessed fluid comprising particulates dispersed within a base fluid into the microchannel;
 (d) separating at least a portion of the particulates from the unprocessed fluid to provide a stream of processed fluid at the fluid outlet; and
 (e) recovering in the collection chamber at least a portion of the particulates initially present in the unprocessed fluid;
 wherein the particulates dispersed in the base fluid together with a portion of the base fluid under the influence of an ambient gravitational field traverse the microporous body and are collected in the collection chamber and are separated from the fluid flowing through the microchannel;
 wherein a first fluid flow having a first flow rate through the microchannel together with the microporous body operationally generate a second fluid flow within the collection chamber as base fluid and particulates traverse the microporous body and enter the collection chamber, and as base fluid re-traverses the microporous body and re-enters the microchannel, the second fluid flow having a flow rate which is a fraction of the first flow rate; and
 wherein at least one of the particulates and the base fluid comprises an organic liquid.

24. The method of claim 23, further comprising a step of priming the device prior to introducing the unprocessed fluid into the microchannel.

25. The method of claim 23, wherein the organic liquid comprises petroleum.

* * * * *